US006524562B2

(12) United States Patent
Guskey

(10) Patent No.: US 6,524,562 B2
(45) Date of Patent: Feb. 25, 2003

(54) SINGLE-PHASE ANTIPERSPIRANT COMPOSITIONS CONTAINING SOLUBILIZED ANTIPERSPIRANT ACTIVE AND SILICONE ELASTOMER

(75) Inventor: Gerald John Guskey, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/735,164

(22) Filed: Dec. 12, 2000

(65) Prior Publication Data

US 2002/0106340 A1 Aug. 8, 2002

(51) Int. Cl.⁷ ............... A61K 7/32; A61K 7/34; A61K 7/38; A61K 7/00
(52) U.S. Cl. .............. 424/65; 424/66; 424/68; 424/400; 424/401
(58) Field of Search ............... 424/65, 66, 68, 424/400, 401

(56) References Cited

U.S. PATENT DOCUMENTS

| 5,654,362 A | 8/1997 | Schulz, Jr. et al. |
| 5,919,437 A | 7/1999 | Lee et al. |
| 5,922,308 A | 7/1999 | Brewster et al. |
| 5,942,215 A | 8/1999 | Edwards et al. |
| 5,968,489 A | 10/1999 | Swaile et al. |
| 5,989,531 A * | 11/1999 | Schamper et al. ............. 424/65 |
| 6,013,248 A | 1/2000 | Luebbe et al. |
| 6,060,546 A | 5/2000 | Powell et al. |
| 6,083,493 A | 7/2000 | Swaile |
| 6,096,298 A | 8/2000 | Swaile |
| 6,103,250 A | 8/2000 | Brieva et al. |
| 6,391,291 B1 * | 5/2002 | Clare et al. ................... 424/65 |
| 6,451,295 B1 * | 9/2002 | Cai et al. ...................... 424/65 |

FOREIGN PATENT DOCUMENTS

| WO | WO99/51192 | 10/1999 |
| WO | WO 00/47184 | 8/2000 |

* cited by examiner

*Primary Examiner*—Jose' G. Dees
(74) *Attorney, Agent, or Firm*—Jack L. Oney

(57) ABSTRACT

Disclosed are antiperspirant and deodorant compositions and corresponding methods of application, wherein the compositions are single-phase systems that comprise a solubilized antiperspirant active, a silicone elastomer and a volatile silicone. These compositions provide improved low residue performance, enhanced stability, and improved cosmetics.

38 Claims, No Drawings

SINGLE-PHASE ANTIPERSPIRANT COMPOSITIONS CONTAINING SOLUBILIZED ANTIPERSPIRANT ACTIVE AND SILICONE ELASTOMER

FIELD OF INVENTION

The present invention relates to antiperspirant compositions, which contain solubilized antiperspirant active, silicone elastomer and a volatile silicone. These compositions are especially useful in providing low-residue performance in combination with improved cosmetics.

BACKGROUND OF THE INVENTION

There are many types of topical antiperspirant products that are commercially available or otherwise known in the antiperspirant art. These products are formulated in a variety of solid, semi-solid and liquid product forms, many of which are also formulated with an emphasis on low-residue performance. In this context, low-residue performance means that the product is applied to the skin with minimal or no visible residue on the applied area. Many of these low-residue products are formulated with solubilized rather than solid antiperspirant active to further improve their low-residue performance. It is well known that the use of solid antiperspirant active in an antiperspirant product can contribute to the appearance of a white, chalky residue when applied to the axilla or other area of the skin.

Although topical products containing solubilized antiperspirant active can provide low-residue performance, they often deliver less desirable cosmetics, e.g., sticky skin feel, and are often more irritating to the skin than many other antiperspirant products containing solid antiperspirant active.

It has now been found that antiperspirant compositions containing solubilized antiperspirant active can be formulated to provide low-residue performance, minimal skin irritation, and good skin cosmetics, provided that such compositions are single-phase systems that also contain a silicone gel material comprising a volatile silicone and a silicone elastomer.

Although silicone elastomers are known for use in antiperspirant compositions, they are typically used in combination with solid rather than solubilized antiperspirant active or they are used in multi-phase emulsions. Moreover, the silicone elastomer compositions disclosed in the antiperspirant art which contain solid antiperspirant active are often associated with higher visible residue after application, and the multi-phase silicone elastomer compositions described in the antiperspirant art have the stability problems commonly associated with multi-phase systems, especially multi-phase emulsions. It has now been found, therefore, that silicone elastomers can be used in combination with solubilized antiperspirant active to deliver low-residue performance and good skin cosmetics, all from a single-phase rather than a multi-phase system.

SUMMARY OF THE INVENTION

The present invention is directed to antiperspirant compositions that are single-phase systems comprising a solubilized antiperspirant active, a silicone elastomer and a volatile silicone. These antiperspirant compositions may also comprise a structurant. The invention is also directed to a method of controlling malodor and perspiration through the application of the antiperspirant composition. The compositions and corresponding methods of the present invention provide improved low residue performance, product stability, antiperspirant efficacy, skin feel performance and/or aesthetics.

DETAILED DESCRIPTION

The antiperspirant compositions of the present invention are single-phase systems that comprise solubilized antiperspirant active, solvent for the antiperspirant active, silicone elastomer, and a volatile silicone. Each of these essential elements is described in detail hereinafter.

The term "single-phase system", as used herein, refers to the antiperspirant compositions of the present invention, wherein all of these compositions are in the form of a solution or microemulsion. In this context, the term "microemulsion" is an art-recognized term that refers to systems other than solutions that behave thermodynamically as a single-phase, i.e., single-phase systems have a single melting temperature, a single refractive index, a single viscosity, and do not readily phase separate.

The term "ambient conditions" as used herein refers to surrounding conditions at about one atmosphere of pressure (1 atm), at about 50% relative humidity, and at about 25° C., unless otherwise specified. All values, amounts and measurements described herein are obtained under ambient conditions, unless otherwise specified.

The term "volatile", as used herein, unless otherwise specified refers to those materials that are liquid under ambient conditions and which have a measurable vapor pressure at 25° C. These materials typically have a vapor pressure greater than about 0.01 mmHg, more typically from about 0.02 mmHg to about 20 mmHg, and an average boiling point typically less than about 250° C., more typically less than about 235° C.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions of the present invention can comprise, consist of, or consist essentially of the essential elements and limitations of the invention described herein, as well as any of the additional or optional ingredients, components, or limitations described herein.

Solubilized Antiperspirant Active

The antiperspirant compositions of the present invention comprise an antiperspirant active suitable for topical application to the skin. The antiperspirant active can be any known or otherwise effective antiperspirant active, provided that the antiperspirant active is solubilized in the composition. The concentration of solubilized antiperspirant active in the composition should be sufficient to provide the desired perspiration wetness and odor control, which will typically range from about 0.1% to about 26%, preferably from about 0.5% to about 20%, more preferably from about 6% to about 20%, by weight of the composition. All such weight percentages are calculated on an anhydrous metal salt basis exclusive of water and any complexing agents such as glycine, glycine salts, or other complexing agents.

Preferred antiperspirant actives for use in the compositions of the present invention include astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

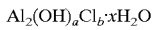

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are described in U.S. Pat. No. 3,887,692 (Gilman, issued Jun. 3, 1975); U.S. Pat. No. 3,904,741 (Jones et. al., issued Sep. 9, 1975) and U.S. Pat. No. 4,359,456 (Gosling et al., issued Nov. 16, 1982), which descriptions are incorporated herein by reference.

Preferred zirconium salts for use in the antiperspirant compositions include those which conform to the formula:

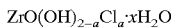

$$ZrO(OH)_{2-a}Cl_a \cdot xH_2O$$

wherein a is any number having a value of from about 0 to about 2; x is from about 1 to about 7; and wherein a and x may both have non-integer values. Particularly preferred zirconium salts are those complexes which additionally contain aluminum and glycine, commonly known as ZAG complexes. These ZAG complexes contain aluminum chlorohydroxide and zirconyl hydroxy chloride conforming to the above-described formulas. Such ZAG complexes are described in U.S. Pat. No. 3,679,068 (Luedders et al., issued Feb. 12, 1974) and U.S. Pat. No. 4,120,948 (Shelton, issued Oct. 17, 1978), which descriptions are incorporated herein by reference.

Solvent for Solubilizing Antiperspirant Active

The antiperspirant compositions of the present invention comprise a solvent for solubilizing the antiperspirant active. The solvent can be any solvent known or otherwise effective in solubilizing or helping to maintain solubilization of the antiperspirant actives described herein, and which is otherwise suitable for topical application to the skin. The solvent can therefore be used to solubilize the antiperspirant active during formulation, or may be added to the composition separate from the solubilized antiperspirant active component with the effect of maintaining or further solubilizing the antiperspirant active in the finished product. The antiperspirant compositions of the present invention comprise solvent for solubilizing the active, wherein the solvent concentration ranges from about 0.1% to about 75%, preferably from about 10% to about 50%, even more preferably from about 15% to about 30%, by weight of the composition. The concentration of the selected solvent will vary depending upon the particular formulation selected, e.g., active concentration selected.

The antiperspirant compositions of the present invention may be aqueous or anhydrous, and therefore the solvent for the antiperspirant active may be aqueous or anhydrous. Both the antiperspirant composition and the solvent are preferably anhydrous. For aqueous embodiments, the antiperspirant compositions may comprise from about 5% to about 75%, preferably from about 10% to about 60%, more preferably from about 15% to about 50%, by weight of water. For anhydrous embodiments, the antiperspirant compositions comprise less than about 5%, preferably less than about 2%, more preferably zero percent, by weight of free or added water.

Suitable solvents for solubilizing the antiperspirant active include water, short chain monohydric alcohols (e.g., C1–C10) such as ethanol, and polyols capable of solubilizing or helping to solubilize the antiperspirant active in the composition. The polyols for use in the antiperspirant composition of the present invention preferably have 2 or more hydroxyl groups with 2 of the hydroxyl groups attached to the α and β carbons of the polyol. The polyols preferably have from about 3 to about 8 carbon atoms, and preferably have either 2 or 3 hydroxyl groups in total.

The polyol solvents for use in the antiperspirant compositions of the present invention are preferably formulated into the composition so that the resulting mole ratio of the polyols to the combination of zirconium and aluminum ions, when such a combination is present in the composition, is at least about 2.0, preferably at least about 2.5, more preferably at least about 3.0. The concentration of antiperspirant active solubilized by the polyols is dependent upon this mole ratio of the 1,2-diols to antiperspirant metal ions (e.g., zirconium and aluminum). Solutions with a mole ratio of polyols to antiperspirant metal ions of less than about 2.0 are unstable and will easily precipitate during the manufacturing process or during storage, so that the maximum concentration of active that should be used to make a stable solution is dependent upon the molecular weight of the polyol solvent, the number of 1,2-diol functional groups per molecule, and the aluminum to zirconium ratio (when present in the composition) making up the active.

The polyol solvents for use in the antiperspirant compositions of the present invention preferably have a ClogP value of less than about 2.0, more preferably from about −4.0 to about 2.0, even more preferably from about −4.0 to about 1.0, even more preferably from about −2.0 to about 1.0, most preferably from about −1.0 to about 0.5. The ClogP values (calculated logP) can be calculated for each polyol by the Pamona Med Chem/Daylight "CLOGP" program, Version 4.42, available from Biobyte Corporation, Claremont, Calif. Other suitable methods for determining ClogP values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, Calif. Daylight V4.61, Algorithm: V3.05, Database: V16. General information pertaining to ClogP values and methodologies are described in Chemical Reviews, 93(4), 1993, 1281–1306, which description is also incorporated herein by reference.

Non-limiting examples of suitable polyol solvents for use herein include any polyol material that is liquid under ambient conditions, or which is otherwise in liquid form within the selected composition, and has the requisite number and arrangement of hydroxyl groups and has the requisite ClogP value as defined herein. Generally, the preferred polyols for selection and use in the composition of the present invention include alkyl diols, glycerol ethers and other polyol liquids, which correspond to the formula:

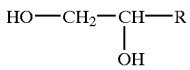

wherein the more preferred polyols have the requisite ClogP and hydroxyl group arrangement as described herein, and wherein R is an alkyl, hydrogen, methyl, hydroxyethyl, ether, ester, amine, amide, alkoxylate, siloxane, functionalized silicone, fluorinated or perfluoroether material, or combination thereof. The R group can be substituted or unsubstituted, branched or straight or cyclic, saturated or unsaturated. The R group is preferably an alkyl group having from 1 to 6 carbon atoms. Non-limiting examples of suitable substituents on the R group include hydroxyl groups, amines, amides, esters, ethers, alkoxylate groups (e.g., ethoxylates, propoxylates, etc.), siloxanes, functionalized silicones, fluorinated or perfluoroether materials, and combinations thereof.

Examples of suitable alkyl diols for use as antiperspirant solvents herein, and their corresponding ClogP values, for use in the antiperspirant composition include 1,2-propanediol (−0.92), glycerin (−1.76), sorbitol (−2.20), 1,2-butanediol (−0.53), 1,2-pentanediol (0.0), 4-methyl-1,2-pentanediol (0.397), 2-methyl-1,2-pentanediol (0.399), 3,3-methyl-1,2-butanediol (0.267), 4-methyl-1,2-hexanediol (0.926), 1,2-heptanediol (1.056), 3-phenyl-1,2-propanediol (0.508), 1,2-hexanediol (0.50), ethylene glycol (−1.3), and combinations thereof.

Suitable glycerol ethers for use as antiperspirant solvents herein, and their respective ClogP values, include glycerol isopropyl ether (−0.51), glycerol propyl ether (−0.73), glycerol ethyl ether (−1.04), glycerol methyl ether (−1.57), glycerol butyl ether (0.01), glycerol isopentyl ether (0.41), diglycerol isopropyl ether (−1.49), diglycerol isobutyl ether (−0.96), diglycerol (−2.95), triglycerol (−3.71), triglycerol isopropyl ether (−2.25), and combinations thereof.

Other suitable polyol liquids, for use as antiperspirant solvents herein, and their respective ClogP values include acetic acid glycerol ester (−1.30), propanoic acid glycerol ester (−0.77), butanoic acid glycerol ester (−0.24), 3-methyl butanoic acid glycerol ester (0.16), 3-trimethylsily-1,2-propane diol (0.56) and combinations thereof. Still other suitable polyols include 1,2,6-hexanetriol (−0.3) and 1,2,4-butanetriol (−1.3).

Preferred polyols for use as antiperspirant solvents herein are 1,2-hexanediol, glycerin, 1,2-propanediol, and combinations thereof, more preferably a combination of two or more of the following solvents: 1,2-hexanediol, glycerin, 1,2-propanediol, ethanol, and water, most preferably an anhydrous combination excluding added water.

Silicone Elastomer

The antiperspirant compositions of the present invention comprise a silicone elastomer suitable for topical application to the skin. The silicone elastomer is incorporated into the antiperspirant compositions in the form of a silicone gel or silicone powder material, wherein the silicone gel or powder comprises a volatile silicone liquid in combination with the silicone elastomer.

The concentration of the silicone elastomer in the antiperspirant compositions of the present invention will vary considerably, depending upon the particular formulation selected and other variables such as the desired viscosity and product form (e.g., solid, semi-solid, liquid), and the primary function to be served by the silicone elastomer. For example, the silicone elastomer can be used at relatively low concentrations in those formulations that are liquid, that contain other additional thickening agents, or which are formulated with the silicone elastomer primarily for cosmetic rather than thickening purposes.

The silicone elastomer concentration in the antiperspirant compositions of the present invention ranges from about 0.1% to about 15%, preferably from about 0.1% to about 10%, more preferably from about 0.5% to about 6%, by weight of the composition. When the silicone elastomer is used primarily for cosmetic purposes, the silicone elastomer concentration in the antiperspirant composition preferably ranges from about 0.1% to about 3%, more preferably from about 0.5% to about 2%, by weight of the compositions. For liquid or semi-solid embodiments, preferably liquid embodiments, the silicone elastomer concentration ranges from about 0.1% to about 10%, preferably from about 0.5% to about 5%, more preferably from about 0.5% to about 2%, by weight of the composition.

Silicone elastomers suitable for use in the antiperspirant compositions of the present invention include any silicone elastomer that is known or otherwise suitable for topical application to the skin. The term "silicone elastomer" as used herein refers to the art-recognized definition of silicone elastomers, which in its broadest reading includes any chemically crosslinked siloxane polymer. No specific restriction exists as to the type of organopolysiloxane that can serve as a starting material for preparing the crosslinked organopolysiloxane (silicone elastomer).

Silicone elastomers for use in the antiperspirant compositions of the present invention can be prepared by any of a variety of methods, including the use of 1) addition reaction-curing organopolysiloxane compositions which cure under platinum metal catalysis by the addition reaction between Si—H containing diorganopolysiloxanes and organopolysiloxanes having silicon-bonded vinyl groups or an organic having vinyl groups; 2) condensation-curing organopolysiloxane compositions which cure in the presence of an organotin compound by a dehydrogenation reaction between hydroxyl-terminated diorganopolysiloxane and Si—H containing diorganopolysiloxanes; 3) condensation-curing organopolysiloxane compositions which cure in the presence of an organotin compound or a titanate ester, by a condensation reaction between a hydroxyl-terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); 4) peroxide-curing organopolysiloxane compositions which thermally cure in the presence of an organoperoxide catalyst; and 5) organopolysiloxane compositions which are cured by high-energy radiation, such as by gamma-rays, ultraviolet radiation, or electron beams.

Addition reaction-curing organopolysiloxane compositions are preferred herein for their rapid curing rates and excellent uniformity of curing. A particularly preferred addition reaction-curing organopolysiloxane composition is prepared from the combination of components (A), (B) and (C), wherein:

(A) can be either:
  (A') which is an organopolysiloxane having at least 2 lower alkenyl groups in each molecule; or
  (A") which is an organic material having at least 2 lower alkenyl groups in each molecule;
(B) is an organopolysiloxane having at least 2 silicon-bonded hydrogen atoms in each molecule; and
(C) is a platinum-type catalyst;

wherein component (A) is the basic component of the silicone elastomer-generating organopolysiloxane, and curing proceeds by the addition reaction of this component with component (B) under catalysis by component (C).

Component (A) as referenced hereinabove contains at least 2 lower alkenyl groups in each molecule, wherein the lower alkenyl groups are preferably vinyl, allyl, or propenyl. While the lower alkenyl groups can be present at any position on the molecule, their presence at the molecular terminals is preferred. The molecular structure of this component may be straight chain, branched straight chain, cyclic, or network, but a straight chain, possibly slightly branched, is preferred. The molecular weight of component (A) is not specifically restricted, and thus the viscosity may range from low viscosity liquids to very high viscosity gums. In order for the cured product to be obtained in the form of a rubbery elastomer, it is preferred that the viscosity at 25° C. be at least 100 centistokes. Non-limiting examples of these organopolysiloxanes (component A') include methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl-(3,3,3-trifluoropropyl) polysiloxanes, and dimethylvinylsiloxy-terminated dimethylsiloxane-methyl(3,3,3-trifluoropropyl)siloxane copolymers.

Non-limiting examples of component (A") include unsaturated materials such as organic dienes, trienes, tetraenes, etc. Examples of dienes include 1,3-butadiene; 1,4-pentadiene; 1,5-hexadiene; 1,6-heptadiene; 1,7-octadiene; 1,8-nonadiene; 1,9-decadiene; 1,10-undecadiene; 1,11-dodecadiene; 1,12-tridecadiene; 1,13-tetradecadiene; etc. such as 1,19-eicosadiene, and other alpha, omega dienes, though the alkenyl group need not be terminal such as 1,4-hexadiene and can be conjugated such as 2,4-hexadiene, and can be branched such as 3-methyl-1,5-hexadiene.

Component (B) as referenced hereinabove is an organopolysiloxane having at least 2 silicon-bonded hydrogen atoms in each molecule and is a crosslinker for component (A). Curing proceeds by the addition reaction of the silicon-bonded hydrogen atoms in this component with the lower alkenyl groups in component (A) under catalysis by component (C). This component (B) must contain at least 2 silicon-bonded hydrogen atoms in each molecule in order to function as a crosslinker. Furthermore, the sum of the number of alkenyl groups in each molecule of component (A) and the number of silicon-bonded hydrogen atoms in each molecule of component (B) is to be at least 5. Values below 5 should be avoided because a network structure is then essentially not formed.

No other specific restriction exists on the molecular structure of component (B) except as otherwise described hereinabove, and it may therefore include straight, branched, or cyclic structures, or combinations thereof. The molecular weight of component (B) is not specifically restricted, but it is preferred that the viscosity of component (B) at 25° C. be from about 1 to about 50,000 centistokes in order to obtain good miscibility with component (A). It is preferred that component (B) be added to component (A) in a quantity such that the molar ratio between the total quantity of silicon-bonded hydrogen atoms and the total quantity of all lower alkenyl groups in component (A) falls within the range of 0.5:1 to 20:1. It is difficult to obtain good curing properties when this molar ratio falls below 0.5:1. When the 20:1 ratio is exceeded, there is a tendency for the hardness to increase to high levels when the cured product is heated. Furthermore, when an organosiloxane containing substantial alkenyl is supplementarily added for the purpose of, for example, reinforcement, it is preferred that a supplemental addition of the SiH-containing component be made in a quantity offsetting these alkenyl groups. Non-limiting examples of component (B) materials include trimethylsiloxy-terminated methylhydrogenpolysiloxanes, trimethylsiloxy-terminated dimethylsiloxane-methylhydrogen-siloxane copolymers, and dimethylsiloxane-methylhydrogen-siloxane cyclic copolymers.

Component (C) as referenced hereinabove is a catalyst of the addition reaction of silicon-bonded hydrogen atoms and alkenyl groups, and includes chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Component (C) as referenced hereinabove is preferably added at from about 0.1 to about 1,000 parts by weight, and more preferably from about 1 to about 100 parts by weight, as platinum-type metal proper per 1,000,000 parts by weight of the total quantity of components (A) plus (B). Other organic groups which may be bonded to silicone in the organopolysiloxane forming the basis for the above-described curable organopolysiloxane compositions are, for example, alkyl groups such as methyl, ethyl, propyl, butyl, hexyl and octyl; substituted alkyl groups such as 2-phenylethyl, 2-phenylpropyl, and 3,3,3-trifluoropropyl; aryl groups such as phenyl, tolyl, and xylyl; substituted aryl groups such as phenylethyl; and monovalent hydrocarbon groups substituted by, for example, the epoxy group, the carboxylate ester group, the mercapto group, the oxyethylene group, the oxypropylone group, the polyoxyethylene group, the polyoxypropylene group, and combinations thereof Non-limiting examples of methods of making organopolysiloxane elastomer powder for use in the antiperspirant compositions of the present invention include the following. An organopolysiloxane composition (i.e., silicone elastomer composition) as described above (e.g., addition-curable, condensation-curable, or peroxide-curable) is mixed with water in the presence of a surfactant (nonionic, anionic, cationic, or amphoteric), and, after mixing to homogeneity in a homomixer, colloid mill, homogenizer, propeller mixer, or other similar device, is cured by discharge into hot water (temperature at least 50° C.) and then dried; the organopolysiloxane composition (addition-curable, condensation-curable, or peroxide-curable) is then cured by spraying it directly into a heated current; the powder is obtained by curing a radiation-curable organopolysiloxane composition by spraying it under high energy radiation; the organopolysiloxane composition (addition-curable, condensation-curable, peroxide-curable) or high energy-curable organopolysiloxane composition is cured, the latter by high energy radiation, and the product is then pulverized using any conventional or otherwise effective pulverizer such as, for example, a ball mill, atomizer, kneader, roll mill, or other similar devices, to thereby form the desired silicone elastomer powder.

The silicone elastomer for use in the antiperspirant composition of the present invention may be emulsifying, non-emulsifying or combinations thereof. The term "non-emulsifying," as used herein refers to those crosslinked organopolysiloxanes from which oxyalkylene units are absent. Non-limiting examples of non-emulsifying silicone elastomers suitable for use in the antiperspirant compositions of the present invention are described in U.S. Pat. No. 6,103,250 (Edwards et al., issued Aug. 24, 1999) and U.S. Pat. No. 5,922,308 (Brewster et al., issued Jul. 13, 1999), which descriptions are incorporated herein by reference. Non-limiting examples of a specific silicone gel material containing a non-emulsifying elastomer for use herein are the cyclomethicone (and) dimethicone crosspolymer available from Dow Corning under the tradename DC-9040, and SFE-168 and SFE-839 available from GE Silicones.

The term "emulsifying," as used herein, refers to those crosslinked organopolysiloxanes having at least one oxyalkylene (e.g., polyoxyethylene or polyoxypropylene) unit. Preferred emulsifying elastomers for use in the antiperspirant compositions of the present invention include polyoxyalkylene-modified elastomers formed from divinyl compounds, particularly siloxane polymers and organic materials with at least two free vinyl groups, reacting with Si—H linkages on a polysiloxane backbone. Non-limiting examples of emulsifying crosslinked organopolysiloxane suitable for use in the antiperspirant compositions of the present invention are described in U.S. Pat. No. 5,412,004 (Tachibana et. al., issued May 2, 1995); U.S. Pat. No. 5,837,793 (Harashima et. al., issued Nov.17, 1998); U.S. Pat. No. 6,103,250 (Brieva et al., issued Aug. 15, 2000); U.S. Pat. No. 5,919,437 (Lee et al., issued Jul. 6, 1999) and U.S. Pat. No. 5,811,487 (Schulz, Jr. et. al., issued Sep. 22, 1998), which descriptions are incorporated herein by reference.

An example of a specific silicone gel material containing an emulsifying silicone elastomer for use herein is the dimethicone (and) dimethicone copolyol crosspolymer available from Shin Etsu under the tradename KSG-21, and DC-9010 and DC-9011 available from Dow Corning.

Non-limiting examples of specific silicone elastomers, silicone elastomer gels, silicone rubber, and silicone elastomer powders, suitable for use in the antiperspirant compositions of the present invention include dimethicone crosspolymer, dimethicone (and) dimethicone copolyol crosspolymer, dimethicone/vinyl dimethicone crosspolymer, cyclomethicone (and) vinyl dimethicone/methicone crosspolymer, crosslinked stearyl methyl dimethyl siloxane copolymer, cetearyl dimethicone/vinyl dimethicone crosspolymer, cyclomethicone [and] dimethicone crosspolymers, and combinations thereof. Such dimethicone/vinyl dimethicone crosspolymers and cyclomethicone (and) dimethicone crosspolymers are supplied by a variety of suppliers including Dow Corning (DC 9506), General Electric (SFE-167, SFE-168, SFE-839), Shin Etsu (KSG-15 [cyclopentasiloxane (and) dimethicone/vinyl crosspolymer], KSG-16 [dimethicone (and) dimethicone/vinyl dimethicone crosspolymer], KSG-17, KSG-18 [phenyltrimethicone (and) dimethicone/phenyl vinyl dimethicone crosspolymer, KSG-20, KSG-21 [dimethicone (and) dimethicone copolyol crossspolymer]), and Grant Industries (Gransil™ line of materials, such as Gransil SR-SYC). Such cyclomethicone [and] dimethicone crosspolymers are supplied by a variety of suppliers including Dow Corning DC 9040. Other silicone elastomers supplied by Dow Corning include DC 9010, DC 9011, DC 9041, DC 9070, DC 9090 and BY29-119.

Other suitable crosslinked organopolysiloxanes and processes for making them are described in U.S. Pat. No. 4,970,252 (Sakuta et al., issued Nov. 13, 1990); U.S. Pat. No. 5,760,116 (Kilgour et al., issued Jun. 2, 1998); and U.S. Pat. No. 5,654,362 (Schulz, Jr. et al. issued Aug. 5, 1997), which descriptions are incorporated herein by reference. The silicone elastomers for use in the antiperspirant compositions of the present invention are preferably cured under anhydrous conditions or in an anhydrous environment. More preferably, the silicone elastomers have one or more moieties such as alkyl, phenyl, styryl, oxyalkylene, polyoxyalkylene, or combinations thereof on either of the (A') or (B) components.

The crosslinked organopolysiloxanes suitable for use in the antiperspirant compositions of the present invention are preferably further processed by subjecting them to high shear processing of at least about 10 psi to about 50,000 psi, preferably from about 10 psi to about 20,000 psi, in the presence of a solvent for the silicone elastomer via a Sonolator or a Gaulin Mill, preferably at less than about 10 passes. Sonolation achieves a resultant composition with silicone elastomer average particle size of preferably at least about 10 microns, more preferably from about 20 microns to about 200 microns, even more preferably from about 30 microns to about 100 microns, even more preferably from about 40 microns to about 95 microns, and most preferably from above 50 microns to about 90 microns, in diameter as measured by a Laser Scattering Particle Size Distribution Analyzer, type LA-910 (available from Horiba; Irvine, Calif.). As used herein, the term "particle size" of the silicone elastomer represents the silicone elastomer particle size in its swelled state in that the silicone elastomer particles have extended beyond their normal size and shape by virtue of their absorption, of the volatile silicone in the antiperspirant composition, as well as any other liquids in the composition that will likewise contribute to the swelling of the elastomers. Viscosity of the silicone elastomer gel preferably ranges from about 10 to about 6,000,000 centipoise (cps), more preferably from about 10 to about 2,000,000 cps, even more preferably from about 100 to about 1,500,000 cps, and even more preferably from about 1,000 to about 1,000,000 cps, as measured at 25° C. by a viscometer, Brookfield LV type (available from Fisher Scientific; Pittsburgh, Pa.) size 4 bar, 60 rpm, 0.3 sec.). Preferably, the silicone elastomers for use in the antiperspirant compositions of the present invention do not undergo recycled processing such as that described in U.S. Pat. No. 5,854,336, Divone, Sr. et al., issued Dec. 29, 1998). In contrast to recycled processing, discrete pass processing as alluded to above ensures that all the particles experience shear as well as the same amount of shear with each run or pass. More specifically, no run or pass is completed until all the particles have experienced the same shear force.

Volatile Silicone Liquid

The antiperspirant compositions of the present invention comprise a volatile silicone liquid in combination with the silicone elastomer described hereinbefore. The volatile silicone liquid suitable for use in the antiperspirant compositions include any silicone material that is known or otherwise suitable for application to the skin, and which has the requisite volatility as defined herein. The volatile silicone liquid can be linear, branched or cyclic.

The concentration of the volatile silicone liquid in the antiperspirant compositions of the present invention ranges from about 0.1% to about 50%, preferably from about 1% to about 30%, more preferably from about 5% to about 20%, by weight of the composition. The volatile silicone liquid can be added to the composition as a separate ingredient, or added as part of a silicone gel or silicone powder material that contains a combination of a silicone elastomer and a volatile silicone liquid.

The volatile silicone liquid for use in the antiperspirant composition is preferably a cyclic silicone having from about 3 to about 7, more preferably from about 5 to about 6, even more preferably 5, silicon atoms. Most preferred are those volatile silicones which conform to the formula:

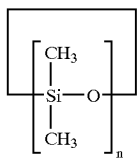

wherein n is from about 3 to about 7; preferably from 5 to 6, most preferably 5. The volatile silicone liquid for use in the antiperspirant composition can also include linear volatile silicones corresponding to the formula

wherein m is from 0 to about 7. The most preferred volatile silicone liquids for use herein include cyclopentasiloxane, cyclohexasiloxane, and combinations thereof. Other volatile silicones include short chain silicones, such as those silicones having the requisite volatility and having a structure characterized as alkyl trimethicones (e.g., caproyl trimethicone), alkyl methicones, alkyl trisiloxanes, or combination thereof. Cyclopentasiloxane is most preferred.

Non-limiting examples of suitable volatile silicone liquids for use in the antiperspirant compositions of the present invention are described in U.S. Pat. No. 4,781,917 (Luebbe et al., issued Nov. 1, 1988), and also described by Todd et al., "Volatile Silicone Fluids for Cosmetics", 91, *Cosmetics and Toiletries*, 27–32, (1976), which descriptions are incorporated herein by reference.

Optional Structurant

The antiperspirant compositions of the present invention may comprise a structurant to help provide the composition with the desired viscosity or product hardness, or to otherwise help suspend any dispersed solids or liquids within the composition. Suitable structurants include any material known or otherwise effective in providing suspending or thickening properties to the composition, or which otherwise provide structure to the final product form. These structurants include gelling agents, and polymeric or non-polymeric or inorganic thickening or viscosifying agents. Such materials will most typically include organic solids (e.g., fatty alcohols, triglycerides and other esters), silicone solids (e.g., silicone waxes, silicone polyethers) crystalline or other wax-type gellants, inorganic particulates such as clays or silicas, or combinations thereof.

The concentration and type of the structurant selected for use in the antiperspirant composition will vary depending upon factors such as the desired product form, viscosity, and hardness. For structurants suitable for use herein, the concentration of such structurant will most typically range from about 0.1% to about 35%, more typically from about 0.1% to about 20%, by weight of the composition. For antiperspirant compositions containing higher silicone elastomer concentrations, or for low-viscosity or other compositions that derive the desired structure primarily from the silicone elastomer gel material itself, these concentrations will more typically range from about 0.1% to about 10%, even more typically from about 3% to about 9%, by weight of the composition.

Suitable gelling agents for use as structurants in the antiperspirant compositions of the present invention include, but are not limited to, solid materials (i.e., solid within the composition under ambient conditions) such as fatty acid gellants, hydroxy acid gellants, esters and amides of fatty acid gellants, esters and amides of hydroxy fatty acid gellants, cholesterolic materials, dibenzylidene alditols, lanolinolic materials, amides (e.g., fatty amides, polyamides), esters (e.g., fatty esters, triglycerides), fatty alcohols, silicone polyethers, natural gums, cellulosic and functionalized cellulosic materials, waxes (e.g. silicone waxes, organic waxes), polymers, n-acyl amino acid derivatives such as n-acyl amino acid amides, n-acyl amino acid esters or amides prepared from glutamic acid, lysine, glutamine, aspartic acid, amides or esters of citric acid, tricarballylic acid, aconitic acid, sucrose esters, alkyl succindiamides, montmorillonite clays, and colloidal, fumed or gelled silicas. Other suitable amide or ester gelling agents are described in U.S. Pat. No. 5,429,816 (Hofrichter et al., issued Jul. 4, 1995) and U.S. Pat. No. 5,840,287 (Guskey et al., issued Nov. 24, 1998), which descriptions are incorporated herein by reference.

Preferred structurants for use herein include materials selected from a variety of chemical groups. Preferred fatty alcohol structurants include cetyl alcohol, myristyl alcohol, stearyl alcohol, 12-hydroxyl stearyl alcohol, and behenyl alcohol. Preferred wax structurants include beeswax, carnauba, baysberry, candelilla, montan, ozokerite, ceresin, hydrogenated castor oil (castor wax), synthetic waxes, and microcrystalline waxes. Preferred hydroxy fatty acid structurants include 12-hydroxystearic acid, 12-hydroxylauric acid, and 16-hydroxyhexadecanoic acid. Preferred fatty acid structurants include behenic acid, eurcic acid, stearic acid, caprylic acid, lauric acid, and isostearic acid. Preferred ester structurants include esters of 12-hydroxystearic acid (e.g., 12-hydroxystearic acid methyl ester), 12-hydroxystearic acid ethyl ester, 12-hydroxystearic acid stearyl ester, 12-hydroxystearic acid benzyl ester, N,N'-12-hydroxyoctadecanoate ethylene glycol, ethylene glycol distearate, sucrose ester of fatty acids (SEFA) (e.g., SEFA behenate). Preferred amide structurants include amides of 12-hydroxystearic acid such as 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, dodecylsuccindibutylamide, and diisopropyl amide of 12-hydroxystearic acid. Preferred cellulosic structurants include hydroxypropylcellulose, hydroxylmethylcellulose, methylcellulose, ethylcellulose, propylcellulose, and hydroxyethylcellulose. Preferred silicone wax structurants include alkylmethyl siloxanes or silicone waxes (such as hexyl, octyl, lauryl, cetyl, cetearyl, stearyl, behenyl, C20–C24, C24–C28, C30–C45); DC-2501 Cosmetic Wax (Dimethicone Copolyol); DC-2502 Fluid (Cetyl Dimethicone); DC-2503 Wax (Stearyl Dimethicone); DC-580 Wax (Stearoxytrimethylsilane [and] Stearyl Alcohol); DC Q5-0158A wax (stearoxytrimethylsilane); AMS C30 Cosmetic Wax (available from Dow Corning); GE SF-1632 (silicone wax); GE SF-1642 (silicone wax); Abil Wax 9810 (silicone wax or C24–28 methicone); Abil Wax 2434 (Stearoxy Dimethicone); Abil Wax 9800 (Stearyl Dimethicone); and Tegomer H—Si 2111, H—Si 2311, A—Si 2120, A—Si 2320, C—Si 2141, C—Si 2341, E—Si 2130, E—Si 2330, V—Si 2150, V—Si 2550, H—Si 6420, H—Si 6440, H—Si 6460 (Alpha-Omega Dimethicone Copolymers); Preferred silicone polyethers are DC 190, DC 193, DC 3225C, DC 5225C, BY 11-030 and modifications (available from Dow Coming); GE SF-1188, SF-1188A, SF-1288, SF-1328 (available from General Electric Silicones); Abil EM-90 and EM-97 (available from Goldschmidt). Preferred triglyceride structurants include tristearin, hydrogenated vegetable oil, trihydroxysterin (Thixcin® R, available from Rheox, Inc.), rape seed oil, fish oils, tripalmiten, tribehenin available as Syncrowax® HRC and Syncrowax® HGL-C (Syncrowax® available from Croda, Inc.). Preferred silica structurants include Cab-O-Sil® (available from Cabot Corp.) and other fumed silica materials. Preferred montmorillonite clay structurants include bentonites, hectorites, and colloidal magnesium aluminum silicates.

Optional Liquid Carrier

The antiperspirant compositions of the present invention may further comprise a liquid carrier in addition to the volatile silicone liquid and the antiperspirant solvent as described hereinbefore. The liquid carrier can be any liquid material that is compatible with the essential ingredients in the composition, and which is otherwise suitable for topical application to the skin. In this context, the optional liquid carrier is any liquid material added to the antiperspirant composition in addition to and other than the volatile silicones and antiperspirant solvents described hereinbefore.

The optional liquid carrier may be added to the antiperspirant compositions of the present invention for any desired purpose, including as emollients, surfactants, solvents, coupling agents, or any other desired purpose. The liquid carrier may be volatile or non-volatile, polar or non-polar, organic or silicone-containing, fluorinated, and/or water-miscible or immiscible. The concentration of the optional liquid carrier in the antiperspirant compositions of the present invention can range from about 0.1% to about 95%, more typically from about 5% to about 60%, even more typically from about 8% to about 40%, by weight of the composition.

Coupling Solvent

The optional carrier liquid can be added to the antiperspirant composition as a coupling solvent to facilitate the compatibility and solubility between the solubilized antiperspirant active component and the volatile silicone liquid, or any other incompatible fluid, all within the composition.

Non-limiting examples of optional liquid carriers as coupling solvents for use in the antiperspirant compositions of the present invention include any of a variety of materials that are liquid under ambient conditions and which are characterized as fatty alcohols, fatty esters, fatty ethers, alcohols, esters, ethers or modified silicones. Preferred organic coupling solvents include octyldodecanol, $C_9$ alcohol, polypropylene glycol-3 myristyl ether (PPG-3 myristyl ether), propylene glycol monoisostearate, dimethyl isosorbide, diisopropyl adipate, isostearyl benzoate, diisopropyl sebacate, polypropylene glycol-10 cetyl ether, propylene glycol isoceteth-3 acetate, myreth-3 octanoate, polypropylene glycol-15 stearyl ether, octylmethoxycinnnamate, polypropylene glycol-14 butyl ether (such as Fluid AP™ from Witco Chemical), ethanol, isopropyl myristate, octyl salicylate, $C_{12}$–$C_{15}$ alkyl benzoate (such as Finsolv TN™ from Finetex), and combinations thereof.

Non-limiting examples of modified silicone liquids for use as coupling solvents in the antiperspirant compositions include those materials that are liquid under ambient conditions and are characterized as methicones, dimethicones, trimethicones and trisiloxanes, preferably those having an oxyalkylene, alkyl, alkylaryl, aryl, hydroxyl, phenyl, and/or styryl moiety attached, non-limiting examples of which include GE CF 1142, GE SF 1023, GE 1205-04-0283, GE 88017, GE SF 1150 (all which are available from General Electric Co.), Masil 756 (available from PPG Specialty Chemicals), Wacker L 066 (available from Wacker Silicones Corp.) and DC 5750 (available from Dow Corning Co.), dimethiconols, silicone polyethers having at least one alkoxylated group.

More preferred among the optional coupling agents for use herein are dimethiconols, silicone polyethers, octyldodecanol, PPG-3 myristyl ether, diisopropyl sebacate, and combinations thereof. Most preferred are octyldodecanol and silicone polyethers.

The silicone polyether as an optional carrier liquid or coupling solvent herein includes those which are alpha-omega (ABA) block copolymers or those which are a dimethicone with appended alkoxylated groups attached to the backbone in a rake, comb or pendant configuration. The silicone polyethers for use herein can contain an ethoxylated $[(EO)_x]$ group, a propoxylated $[(PO)_y]$ group, or a combination thereof $[(EO)_x(PO)_y]$, wherein x and y can be non-integers and are independently 0 to about 50, with x+y being from about 1 to about 100, preferably from about 1 to about 40, more preferably from about 2 to about 20, and even more preferably from about 4 to about 12, most preferably, y=0 and the silicone polyethers are ABA block copolymers. In addition, the molecular weight of the selected silicone polyether as a carrier liquid or coupling solvent is preferably greater than about 1,000 atomic mass units (amu). Non-limiting examples of specific silicone polyethers suitable for use herein include those that have alkoxylated groups such as $(EO)_7$, $(EO)_{19}(PO)_{19}$, $(EO)_{10}(PO)_4$, $(EO)_{12}$, $(PO)_{2.3}$, and/or $(EO)_4$.

The dimethicone backbone of the silicone polyether liquid carrier, wherein the polyether is characterized as a rake, comb or pendant configuration, has an MDD'M structure wherein D is $—[(CH_3)_2Si—O]_z—$, D' is $—[(\{CH_3\}\{R\})—Si—O]_z—$ wherein R is $[(EO)_x(PO)_y]$, and the M is $[(CH_3)_3Si—O]_z$ with z being from about 1 to about 1000, preferably from about 10 to about 100, more preferably from about 20 to about 40. Non-limiting examples of specific polymers include $(EO)_7D_{35}(EO)_7$, $(EO)_7MD_{32}M(EO)_7$, $(EO)_{12}$-$MD_{32}M(EO)_{12}$, $(EO)_{12}$-DD'-$(EO)_{12}$, $(EO)_7$-DD'$(EO)_7$, wherein D/D' ratios are 1 to 500, preferably 1 to 100, more preferably 2 to 40, even more preferably 5 to 15. Alkoxylated materials can be endcapped with an OH or other oxyalkylated group such as methoxy, ethoxy, acetoxy, etc., with OH terminated being the most preferred.

Other non-limiting examples of specific silicone polyether liquid carriers for use herein include $MD_{8.7}D'_{3.7}M$ with $(EO)_4$, $(EO)_7$ or $(EO)_{12}$; $MD_{13.5}D'_2M$ with $(EO)_4$, $(EO)_7$ or $(EO)_{12}$; $MD_{14.4}D'_{1.8}M$ with $(EO)_4$ to $(EO)_{12}$; $MD_{103}D'_{0.5}M$; $MD_{157}D'_{21}M$; $MD_{557}D'_{13}M$ with (PO), with y from 1 to 12; $M'D_{8.2}M'$ with $(EO)_x$ with x from 1 to 12.

Non-Volatile Silicone Liquid

The optional liquid carrier of the antiperspirant composition of the present invention may comprise a non-volatile silicone liquid. Non-limiting examples of non-volatile silicone liquids for use herein include modified silicone carriers, provided that such carriers are liquid under ambient conditions, are not volatile as defined herein, and have a viscosity of from about 5 centistokes to about 100,000 centistokes, preferably less than about 10,000 centistokes, more preferably from about 10 centistoke to about 1,000 centistokes, and even more preferably from about 10 centistoke to about 100 centistokes. These modified silicone carriers are generally known in the chemical arts, some examples of which are described in *Cosmetics, Science and Technology* 27–104 (M. Balsam and E. Sagarin ed. 1972); U.S. Pat. No. 4,202,879 (Shelton, issued May 13, 1980) and U.S. Pat. No. 5,084,577 (Bolich, issued Jan. 28, 1992), which descriptions are incorporated herein by reference.

The modified silicone liquid carriers suitable for use in the antiperspirant compositions include, but are not limited to, compounds or materials as defined hereinabove and which are generally characterized as follows: silicone polyethers or silicone glycols (such as dimethicone copolyol); silicone alkyl-inked polyethers (such as Goldschmidt Abil EM-90 or Abil EM-97); siloxane surfactants of a pendant/rake/comb configuration, silicone surfactants of a trisiloxane configuration, and silicone surfactants of ABA/alpha-omega block copolymers (such as polyoxyalkylenes, polyoxyethylene or ethoxylated, polyoxypropylene or oxypropylene, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, hydroxyl, hydroxyalkyl, polyhydroxy alkyl, alkyl, methyl, amino, trifluoropropyl, vinyl, alkoxy, arylalkyl, aryl, phenyl, styryl, polyethers, esters, carboxylics; nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxymethoxytrisiloxane; silicone emulsifiers; silicone or siloxane resins, alkyl silicone resins, polyoxyalkylene silicone resins; MQ resins, alkoxysiloxanes; alkoxysilanes; methicones; and combinations thereof.

Non-limiting examples of suitable modified silicone carriers for use in antiperspirant compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520; DC-593 Fluid (Dimethicone [and] Trimethylsiloxysilicate); DC-3225C or DC-5225C Fluid (Cyclomethicone [and] Dimethicone Copolyol); DC-190 Fluid (Dimethicone Copolyol); DC-193 Fluid (Dimethicone Copolyol); BY-11-030 (Cyclomethicone [and] Dimethicone Copolyol); DC-1732, DC-5732, DC-5750, DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-1-3563 (Dimethiconol); DC-X2-1286 (Dimethiconol); DC-X2-1146A (Cylcomethicone [and] Dimethiconol); DC-8820 Fluid (Amino functionalized); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate); and combinations thereof.

Other non-limiting examples of suitable modified silicone carriers for use in the antiperspirant compositions herein include the following modified silicones available from General Electric: GE SF-1023 (Dimethyl-Diphenyl-Siloxane); GE SF-1066, GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1188 (Dimethicone copolyol); GE SF-1188A (Silicone polyether copolymer); GE SF-1288 (silicone polyether copolymer, dimethyl-methyl 3-hydroxypropyl ethoxylated siloxane); GE SF-1318 (methylester siloxane); GE SF-1328 (silicone surfactant, dimethyl-methyl 3-hydroxypropyl ethoxylated-propoxylated siloxane); GE SF-1550 (methylphenyl siloxane, hexamethyl-3-phenyl-3-[[trimethylsilyl]oxy] trisiloxane); GE SS-4267 (Dimethicone [and] Trimethylsiloxysilicate) and combinations thereof.

Other non-limiting examples of suitable modified silicone carriers for use in the antiperspirant compositions herein include the following: Masil 756 from PPG Specialty Chemicals (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Unisil SF-R (dimethiconol from UPI); Silicate Cluster from Olin (Tris[tributoxysiloxy] methylsilane); silicone copolymer F-754 (dimethicone copolyol from SWS Silicones); and combinations thereof.

The optional carrier liquid can also include non-volatile linear silicones which include, but are not limited to, those which conform to either of the formulas:

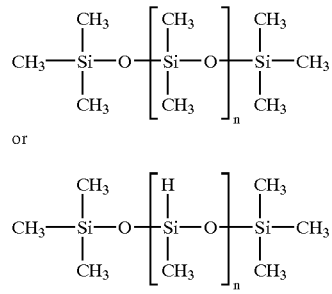

or wherein n is greater than or equal to about 8. These linear silicone materials will generally have viscosity values of from about 10 centistokes to about 100,000 centistoke, preferably from about 20 centistokes to about 500 centistoke, more from about 10 centistoke to about 50 centistoke, as measured under ambient conditions. Examples of non-volatile, linear silicones suitable for use in the antiperspirant compositions include, but are not limited to, Dow Corning 200, Rhodorsil Oils 70047 available from Rhone-Poulenc, Masil SF Fluid available from PPG Specialty Chemicals, Dow Corning 225, and SF-96 Silicone Fluids (available from G.E. Silicones).

Volatile, Nonpolar Hydrocarbon Liquid

The optional liquid carrier may also comprise a volatile, nonpolar hydrocarbon liquid, including volatile branched chain hydrocarbons having from about 4 to about 30 carbon atoms, preferably from about 4 to about 20 carbon atoms, more preferably from about 6 to about 20 carbon atoms, non-limiting examples of which include the isoparaffins available from Exxon Chemical Company (Baytown, Tex. U.S.A.), as Isopar M (C13–C14 Isoparaffin), Isopar C (C7–C8 Isoparaffin), Isopar E (C8–C9 Isoparaffin), Isopar G (C10–C11 Isoparaffin), Isopar L (C11–C13 Isoparaffin), Isopar H (C11–C12 Isoparaffin), and combinations thereof. Other non-limiting examples of suitable branched chain hydrocarbons include Permethyl 99A (isododecane), Permethyl 102A (isoeicosane), Permethyl 101A (isohexadecane), and combinations thereof. The Permethyl series are available from Presperse, Inc. (South Plainfield, N.J., U.S.A.). Other non-limiting examples of suitable branched chain hydrocarbons include petroleum distillates such as those available from Phillips Chemical as Soltrol 130, Soltrol 170, and those available from Shell as Shell Sol 70, –71, and –2033.

Non-limiting examples of other suitable nonpolar, volatile hydrocarbon liquids include dodecane, octane, decane, hydrogenated polyisobutanes and combinations thereof, and the Norpar™ series of paraffins available from Exxon Chemical Company such as Norpar 12, –13, and –15. Yet another example includes C11–C15 alkanes/cycloalkanes, such as those available from Exxon as ExxSol™ D80.

Non-Volatile, Nonpolar Hydrocarbon Liquid

The optional liquid carrier in the antiperspirant compositions of the present invention may comprise a non-volatile, nonpolar liquid, non-limiting examples of which include mineral oil, petrolatum, and certain other branched-chain, non-volatile hydrocarbons. Mineral oils useful in the antiperspirant compositions of the present invention include petroleum derivatives which are complex mixtures of paraffinic and naphthenic (cyclic) hydrocarbons. These include both "light" and "heavy" mineral oils, which are differentiated on the basis of the average molecular weight of the hydrocarbons included. The mineral oils useful herein have the following properties: viscosity of from about 5 centistokes to about 70 centistokes at 40° C.; density between about 0.82 and about 0.89 $g/cm^{0.3}$ at 25° C.; and flash point between about 138° C. and about 216° C.

The branched chain hydrocarbons useful as carrier liquids herein are typically highly-branched, non-volatile aliphatic liquids containing an average of from about 16 to about 68, preferably from about 20 to about 40, carbon atoms.

Fluorochemical Liquid

The optional carrier liquid may also comprise fluorochemicals such as fluorotelemers and/or perfluoropolyethers, some examples of which are described in "Using Fluorinated Compounds in Topical Preparations", 111, *Cosmetics & Toiletries*, 47–62, (October 1996) which descriptions are incorporated herein by reference. More specific examples of suitable fluorochemicals include, but are not limited to, perfluoroethers, perfluoropolymethyl isopropyl ethers, perfluoropolypropylethers, acrylamide fluorinated telomer, fluorinated amide surfactants, perfluorinated thiol surfactants, and combinations thereof. Other suitable fluorochemicals include polyperfluoroisopropyl ethers available from Dupont Performance Chemicals under the trade name Fluortress® PFPE oils, and/or the fluorosurfactants from Dupont Performance Chemicals under the trade name Zonyl® Fluorosurfactants. Still other suitable fluorochemicals for use herein include hydrofluoroethers such as Extractive 7100 (available from 3M), FPE and RfoMe fluids (available from Daikin, Japan), and the Flutec™ series (available from Cosmetic Innovations and Technologies, Nord, France).

Deodorant Active

The antiperspirant compositions of the present invention may comprise deodorant actives. These deodorant actives may be used in addition to or in place of some or all of the antiperspirant active material, and include any known or otherwise safe and effective deodorant active suitable for topical application to the skin.

Deodorant actives suitable for use in the composition of the present invention include any topical material that is known for or otherwise effective in preventing or eliminating malodor associated with perspiration, preferably antimicrobial deodorant actives.

Antimicrobial deodorant actives suitable for use herein include cetyl-trimethylammonium romide, cetyl pyridinium chloride, benzethonium chloride, diisobutyl phenoxy ethoxy ethyl imethyl benzyl ammonium chloride, sodium N-lauryl sarcosine, sodium N-palmethyl sarcosine, auroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether, 3,4,4'-trichlorocarbanilide, diaminoalkyl amides such as L-lysine hexadecyl amide, heavy metal salts of citrate, salicylate, and piroctose, especially zinc salts and acids thereof, heavy metal salts of pyrithione, especially zinc pyrithione, zinc phenolsulfate, farnesol, octoxyglycerin and combinations thereof. Preferred antimicrobial agents are 2,4,4'-trichloro-2'-hydroxy diphenyl ether (triclosan) and/or 3,4,4'-trichlorocarbanilide (triclocarban).

The concentration of the deodorant active in the composition ranges from about 0.01% to about 10%, preferably from about 0.1% to about 5%, more preferably from about 0.1% to about 1%, by weight of the composition.

Other Optional Ingredients

The antiperspirant compositions of the present invention may further comprise other optional ingredients to modify the physical, chemical, cosmetic or aesthetic characteristics of the compositions or to serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Non-limiting examples of other optional ingredients suitable for use in the antiperspirant compositions herein include fragrances, pH buffering agents, soothing agents, dyes and pigments, medicaments, propellants, baking soda and related materials, preservatives, and combinations thereof.

Method of Manufacture

The compositions of the present invention may be made by any of the methods known in the art for formulating antiperspirant and/or silicone elastomer compositions, or which are otherwise effective in formulating such compositions. As will be apparent to those skilled in the art, the particular method will be dependent upon factors such as the specific types and amounts of components employed as well as the final product form and product characteristics. Specific non-limiting examples of such methods are described hereinafter.

Product Form

The antiperspirant compositions of the present invention can be formulated in any liquid, solid, semi-solid form, provided that the selected form is a single-phase system and contains all of the essential elements as defined herein. These compositions can be formulated as opaque, translucent or clear formulations, preferably as translucent or clear formulations. The compositions are preferably formulated as liquids, semi-solids or gels, more preferably liquids, and even more preferably as clear or translucent liquids.

The antiperspirant compositions of the present invention are preferably packaged into any container or applicator suitable for use in applying the composition to the axilla or other suitable area of the skin. For the preferred liquid embodiments of the present invention, the antiperspirant composition is preferably packaged into a porous dome applicator. A non-limiting example of a porous dome applicator suitable for use herein is disclosed in U.S. Pat. No. 4,936,700 (Morris, issued Jun. 26, 1990), which description is incorporated herein by reference.

Method for Use

The antiperspirant compositions of the present invention are formulated in final form to be topically applied to the axilla or other area skin to control malodor and perspiration. These methods comprise applying to the axilla or other area of the skin a safe and effective amount of the antiperspirant composition of the present invention. In this context, the term "safe and effective amount" means an amount of the antiperspirant composition topically applied to the skin that is effective in inhibiting or minimizing odor and perspiration at the site of application while also being safe for topical use at a reasonable risk/benefit ratio. In this context, a safe and effective amount typically ranges from about 0.1 gram per axilla or other area of the skin to about 2.0 gram per axilla or other area of the skin, preferably from about 0.5 gram to about 1.0 gram per axilla or other area of the skin. The compositions are preferably applied to the axilla one or more times daily, preferably once daily.

EXAMPLES

The following Examples 1–26 illustrate specific embodiments of the antiperspirant compositions and methods of the present invention, but are not intended to be limiting thereof. Other modifications can be undertaken by the skilled artisan without departing from the spirit and scope of this invention.

Each of the exemplified compositions is applied topically to the axilla in an amount effective to inhibit or prevent perspiration, typically an amount ranging from about 0.1 gram to about 2.0 grams per axilla. The applied compositions are effective in inhibiting perspiration and malodor from the applied areas, have good skin feel characteristics during and after application, and leave little or no visible residue on the skin. The applied compositions are mild to the skin and cause little or no skin irritation. All exemplified amounts are weight-weight percentages based upon the total weight of the composition, unless otherwise specified.

Each of the exemplified compositions (1–26) can be prepared by first solubilizing the antiperspirant active in the selected solvent (or obtaining antiperspirant active in solubilized form), placing the solubilized antiperspirant active in an appropriate vessel, adding and mixing together any optional liquid until a homogeneous mixture is formed. The volatile silicone fluid is placed in a separate vessel and mixed together with the silicone elastomer, which may be in the form of a liquid, gel, or powder, until a dispersed and homogenous mixture is formed. The volatile silicone/silicone elastomer combination is passed through a high shear mixer to form a uniform and homogenous composition. The number of passes through the high shear mixer will depend on the pressure, which in turn depends on the type of high shear equipment used. Typically, one to three passes are completed using a Gaulin Mill high shear mixer (available from Fisher Scientific, Pittsburgh, Pa.) with a 0.001 inch slit orifice at about 5,000 psi at ambient temperature. This sheared composition is then combined with the antiperspirant active solution in the first vessel and mixed together until a dispersed and homogenous composition is formed. The resulting composition is passed again through a high shear mixer as described above. All other optional ingredients are then added to the mixture and subjected to high shear, if necessary. If an optional structurant is added, at this point the composition is heated with all components (except any fragrances, dyes, deodorant actives, or other heat sensitive materials) until the structurant has been melted. The melting point of most suitable structurants will typically range from about 40° C. to about 150° C. Then, the final ingredients are added (such as any fragrances, dyes, deodorant actives, or other heat sensitive materials) and subsequently cooled to just about above the solidification temperature of the composition, typically to about 40° C. to about 70° C. The resultant composition is dispensed into an appropriate package. Unless otherwise specified, all process steps described herein are performed under ambient conditions.

As an example, the composition described in Example 1 is formulated by first preparing a 30% antiperspirant active solution using a 1,2-hexanediol solvent to solubilize the active. Preparation of solubilized active is disclosed in U.S. Pat. No. 5,968,489 (Swaile et al, issued Oct. 19, 1999), which disclosure is incorporated herein by reference. The antiperspirant active solution is then placed in an appropriate vessel, and 20 parts of additional 1,2-hexanediol solvent is added to make a 25% active/1,2-hexanediol solution. The diluted active solution is mixed thoroughly at 500 revolutions per minute (rpm) for 30 minutes, using a twin turbine blade, until a clear solution is formed. In a separate vessel, 60 parts of this diluted active solution and 15 parts of octyldodecanol are combined and mixed thoroughly together (500 rpm, 30 minutes) before adding 19 parts cyclopentasiloxane with mixing (500 rpm, 30 additional minutes). Fragrance at 1 part is then added to this mixture and mixed thoroughly (500 rpm, 5 minutes). Then, 5 parts DC 9040 silicone elastomer (which is about 10% silicone elastomer solids, providing 0.5% non-emulsifying silicone elastomer to the mixture) is added to this mixture, mixing at 500 rpm for 60 minutes. In this particular example, all process steps are performed under ambient conditions, unless otherwise specified. The resultant composition is dispensed into an appropriate package.

In yet another example, the composition described in Example 5 is formulated by first preparing a 30% antiperspirant active solution using glycerin as the antiperspirant solvent. The resulting antiperspirant solution is then placed in an appropriate vessel, and 20 parts of additional glycerin is added to the active solution to make a 25% active/glycerin solution. The diluted active solution is mixed thoroughly at 500 rpm for 30 minutes, using a twin turbine blade (IKA Labortechnik type, available from Janke & Kunzel, GmbH & Co., Germany), until a uniform mixture is formed. In a separate vessel, 60 parts of the diluted active solution and 25 parts of a silicone polyether are combined and mixed thoroughly (500 rpm, 30 minutes) before adding 9.5 parts cyclopentasiloxane with agitation (500 rpm, 30 minutes) followed by 0.5 part fragrance with agitation (500 rpm, 5 minutes). To the fragrance-containing mixture is added 5 parts KSG-21 (from Shin-Etsu) silicone elastomer (which is about 10% silicone elastomer solids, providing 0.5% emulsifying silicone elastomer to the mixture) is added to this mixture with agitation (500 rpm, 60 minutes). The resulting composition is subjected to high shear for 1 pass through a Gaulin Mill at an approximate pressure of about 5,000 psi. In this particular example, all process steps are performed under ambient conditions, unless otherwise specified. The resultant composition is dispensed into an appropriate package.

The compositions described in Examples 1–7 are also packaged in a porous dome applicator. The compositions are clear to translucent in appearance and are applied to the axilla by the methods described above.

TABLE I

Liquid Antiperspirant Compositions.

| Ingredient | Ex. 1 | Ex. 2 | Ex. 3 | Ex. 4 | Ex. 5 | Ex. 6 | Ex. 7 |
|---|---|---|---|---|---|---|---|
| 1,2-hexanediol | 45 | 20 | 30 | 45 | — | 40 | 45 |
| Glycerin | — | — | 30 | — | 45 | 40 | — |
| Aluminum/zirconium trichlorohydrex gly (% by weight powdered active, solubilized in solvent) | 15 | — | 15 | — | 15 | — | 15 |
| Aluminum/zirconium tetrachlorohydrex gly (% by weight powdered active, solubilized in solvent) | — | 10 | — | 15 | — | 10 | — |
| DC 9040 [Dow Corning] | 0.5 | — | — | — | — | — | 0.5 |
| SF 1229 [GE Silicones] | — | 0.1 | — | — | — | — | — |
| Cetearyl dimethicone/vinyl dimethicone | — | — | 0.5 | — | — | — | — |
| Gransil SR-SYL [Gransil Industries] | — | — | — | 0.1 | — | — | — |
| KSG-21 [Shin Etsu] | — | — | — | — | 0.5 | — | — |
| DC 9010 [Dow Corning] | — | — | — | — | — | 2 | — |
| Cyclopentasiloxane (D5) | 23.5 | 0.4 | 5 | 23.9 | 14.0 | 8 | 17.5 |
| Octyldodecanol | 15 | — | — | 15 | — | — | — |
| PEG-8 | — | 69 | — | — | — | — | — |
| Silicone Polyether | — | — | 19.5 | — | 25 | — | 20 |
| Hydroxyethylcellulose | — | — | — | — | — | — | 1 |
| Fragrance | 1 | 0.5 | — | 1 | 0.5 | — | 1 |

TABLE II

Gel/Semi-solid Antiperspirant Compositions.

| Ingredient | Ex. 8 | Ex. 9 | Ex. 10 | Ex. 11 | Ex. 12 | Ex. 13 |
|---|---|---|---|---|---|---|
| 1,2-hexanediol | 45 | 45 | 40 | 30 | 29.7 | — |
| Glycerin | — | — | — | 25 | 20 | 30 |
| Aluminum/zirconium trichlorohydrex gly (% by weight powdered active, solubilized in solvent) | 5 | — | 10 | — | — | — |
| Aluminum/zirconium tetrachlorohydrex gly (% by weight powdered active, solubilized in solvent) | — | 5 | — | 15 | — | 10 |
| Triclosan | — | — | — | — | 0.3 | — |
| KSG-21 [Shin Etsu] | 6 | — | — | — | — | — |
| Cyclomethicone (and) dimethicone crosspolymer | — | 6 | — | — | — | — |
| Dimethicone crosspolymer [Dow Corning] | — | — | 6 | — | — | — |
| SF 1229 [GE Silicones] | — | — | — | 5 | — | — |
| Crosslinked stearyl methyl dimethyl siloxane copolymer | — | — | — | — | 5 | — |
| DC 9011 [Dow Corning] | — | — | — | — | — | 5 |
| Cyclopentasiloxane (D5) | 19 | 19.5 | 10 | 24 | 19.5 | 20 |
| Diisopropyl sebacate | — | 20 | — | — | — | — |
| Octyldodecanol | 24 | 4 | — | — | — | — |
| PPG-3-myristyl ether | — | — | 34 | — | — | — |
| PEG-8 | — | — | — | — | — | 20 |
| Silicone polyether | — | — | — | — | 25 | 15 |
| Fragrance | 1.0 | 0.5 | — | 1.0 | 0.5 | — |

TABLE III

Gel/Semi-solid Antiperspirant Compositions.

| Ingredient | Ex. 14 | Ex. 15 | Ex. 16 | Ex. 17 | Ex. 18 | Ex. 19 |
|---|---|---|---|---|---|---|
| 1,2-hexanediol | 45 | 45 | 40 | 30 | 29.7 | — |
| Glycerin | — | — | — | 25 | 20 | 20 |
| Aluminum/zirconium trichlorohydrex gly (% by weight powdered active, solubilized in solvent) | 10 | — | 10 | — | — | — |
| Aluminum/zirconium tetrachlorohydrex gly (% by weight powdered active, solubilized in solvent) | — | 10 | — | 15 | — | 10 |
| Triclosan | — | — | — | — | 0.3 | — |

TABLE III-continued

Gel/Semi-solid Antiperspirant Compositions.

| Ingredient | Ex. 14 | Ex. 15 | Ex. 16 | Ex. 17 | Ex. 18 | Ex. 19 |
|---|---|---|---|---|---|---|
| KSG-21 [Shin Etsu] | 1 | — | — | — | — | — |
| Cyclomethicone (and) dimethicone crosspolymer | — | 1 | — | — | — | — |
| Dimethicone crosspolymer [Dow Corning] | — | — | 2 | — | 0.5 | — |
| SF 1229 [GE Silicones] | — | — | — | 0.5 | — | — |
| Crosslinked stearyl methyl dimethyl siloxane copolymer | — | — | — | — | 0.5 | — |
| DC 9011 [Dow Corning] | — | — | — | — | — | 4 |
| Cyclopentasiloxane (D5) | 17 | 17 | 9 | 10 | 18.5 | 11 |
| Dibenzylidene sorbitol (DBS) | 2 | — | — | — | — | — |
| Stearyl alcohol | — | — | 10 | — | — | — |
| N,N'-12-hydroxyoctadecanoate ethylene glycol | — | — | — | 5 | — | — |
| Diisopropyl sebacate | 20 | — | — | — | — | 20 |
| Octyldodecanol | 4 | 24 | — | — | — | 5 |
| PPG-3-myristyl ether | — | — | 29 | — | — | — |
| PEG-8 | — | — | — | — | — | 28 |
| Silicone polyether | — | — | — | 13.5 | 29 | — |
| SEFA Behenate | — | 2.5 | — | — | — | — |
| Hydroxy propyl cellulose | — | — | — | — | 1 | 2.0 |
| Fragrance | 1 | 0.5 | — | 1 | 0.5 | — |

TABLE IV

Solid Antiperspirant Compositions.

| Ingredient | Ex. 20 | Ex. 21 | Ex. 22 | Ex. 23 | Ex. 24 | Ex. 25 | Ex. 26 |
|---|---|---|---|---|---|---|---|
| 1,2-hexanediol | 35 | 30 | — | — | 30 | 45 | — |
| Glycerin | — | — | 20 | 20 | 30 | — | 45 |
| Aluminum/zirconium trichlorohydrex gly (% by weight powdered active, solubilized in solvent) | 15 | — | 12 | — | 15 | — | 15 |
| Aluminum/zirconium tetrachlorohydrex gly (% by weight powdered active, solubilized in solvent) | — | 15 | — | 12 | — | 15 | — |
| KSG-21 [Shin Etsu] | 10 | — | — | — | — | — | — |
| SF 1229 [GE Silicones] | — | 10 | — | — | — | — | — |
| Cyclomethicone (and) dimethicone crosspolymer | — | — | 10 | — | 0.5 | — | 1 |
| Dimethicone crosspolymer [Dow Corning] | — | — | — | 10 | — | 2 | — |
| Silicone polyether | 20 | 20 | 20 | 20 | 9.5 | — | 25 |
| Stearyl alcohol | — | — | — | — | 10 | — | — |
| N,N'-12-hydroxyoctadecanoate ethylene glycol | — | — | — | — | — | 10 | — |
| Cyclopentasiloxane (D5) | 19 | 19.5 | 20 | 19 | 5.0 | 12 | 12.5 |
| Octyldodecanol | — | — | — | — | — | 15 | — |
| PEG-8 | — | 5 | 18 | 18 | — | — | — |
| Hydroxy propyl cellulose | — | — | — | — | — | — | 0.5 |
| Fragrance | 1 | 0.5 | — | 1 | — | 1 | 1 |

What is claimed is:

1. An antiperspirant composition comprising:
a) a solubilized antiperspirant active;
b) a solvent for solubilizing the antiperspirant active;
c) a silicone elastomer; and
d) a volatile silicone,
wherein the silicone elastomer is formulated such that the antiperspirant composition is a single-phase system.

2. A composition according to claim 1, wherein the composition is anhydrous.

3. An antiperspirant composition according to claim 1, wherein the composition comprises from about 0.1% to about 30% by weight of the antiperspirant active, from about 0.1% to about 75% by weight of the solvent for solubilizing the antiperspirant active, from about 0.1% to about 15% by weight of the silicone elastomer, and from about 0.1% to about 50%, by weight of the volatile silicone.

4. An antiperspirant composition according to claim 3, wherein the composition comprises from about 6% to about 20% by weight of the antiperspirant active.

5. An antiperspirant composition according to claim 3, wherein the composition comprises from about 15% to about 30% by weight of the solvent to solubilize the antiperspirant active.

6. An antiperspirant composition according to claim 3, wherein the composition comprises from about 0.5% to about 6% by weight of the silicone elastomer.

7. An antiperspirant composition according to claim 6, wherein the composition comprises from about 0.5% to about 2% by weight of the silicone elastomer.

8. An antiperspirant composition according to claim 3, wherein the composition comprises from about 5% to about 20% by weight of the volatile silicone.

9. An antiperspirant composition according to claim 3, wherein the silicone elastomer is an emulsifying crosslinked organopolysiloxane.

10. An antiperspirant composition according to claim 3, wherein the silicone elastomer is a non-emulsifying crosslinked organopolysiloxane.

11. An antiperspirant composition according to claim 3, wherein the composition further comprises from about 0.1% to about 95% by weight of a liquid carrier other than and in addition to the volatile silicone and the solvent for the antiperspirant active.

12. An antiperspirant composition according to claim 11, wherein the liquid carrier comprises a coupling solvent.

13. An antiperspirant composition according to claim 3, wherein the composition further comprises from about 0.1% to about 35%, by weight of a structurant.

14. An antiperspirant composition according to claim 13, wherein the composition comprises from about 0.1% to about 20% by weight of the structurant.

15. Antiperspirant composition according to claim 4, wherein the solubilized antiperspirant active is selected from the group consisting of aluminum salts, zirconium salts, and combinations thereof.

16. Antiperspirant composition according to claim 15, wherein the solubilized antiperspirant active is aluminum/zirconium trichlorohydrex glycine.

17. An antiperspirant composition according to claim 5, wherein the solvent has a ClogP of less than or equal to about 2.

18. An antiperspirant composition according to claim 17, wherein the solvent has a ClogP of less than or equal to about 0.

19. An antiperspirant composition according to claim 9, wherein the silicone elastomer is a cyclomethicone [and] dimethicone crosspolymer, a dimethicone/vinyl dimethicone crosspolymer, or a combination thereof.

20. An antiperspirant composition according to claim 10, wherein the silicone elastomer is a cyclomethicone and vinyl dimethicone/methicone crosspolymer, a crosslinked stearyl methyl dimethyl siloxane copolymer, or a combination thereof.

21. An antiperspirant composition according to claim 19, wherein the silicone elastomer is a crosslinked organopolysiloxane with an alkyl, aryl, alkylaryl, styryl, phenyl or ester group.

22. An antiperspirant composition according to claim 20, wherein the silicone elastomer is a crosslinked organopolysiloxane with an alkyl, aryl, alkylaryl, styryl, phenyl or ester group.

23. An antiperspirant composition according to claim 8, wherein the volatile silicone is selected from the group consisting of cyclopentasiloxane, cyclohexasiloxane, and mixtures thereof.

24. An antiperspirant composition according to claim 13, wherein the structurant is selected from the group consisting of hydroxy acid gellants, esters and amides of fatty acid gellants, esters and amides of hydroxy fatty acid gellants, dibenzylidene alditols, amides, esters, fatty alcohols, silicone waxes, silicone polyethers, cellulosic and functionalized cellulosic materials, waxes, sucrose esters, and combinations thereof.

25. An antiperspirant composition according to claim 1, wherein the composition is a solid.

26. An antiperspirant composition according to claim 1, wherein the composition is a liquid.

27. An antiperspirant composition according to claim 1, wherein the composition is a semi-solid.

28. An antiperspirant composition comprising from about 6% to about 26% by weight of solubilized aluminum/zirconium trichlorohydrex glycine, about 30% to about 45% by weight of 1,2-hexanediol, from about 0.1% to about 6% by weight of emulsifying silicone elastomer, from about 10% to about 30% by weight of cyclopentasiloxane, and from about 8% about 40% by weight of silicone polyether.

29. An antiperspirant composition comprising from about 6% to about 26% by weight of solubilized aluminum/zirconium trichlorohydrex glycine, about 30% to about 45% by weight of glycerin, from about 0.1% to about 6% by weight of emulsifying silicone elastomer, from about 1% to about 20% by weight of cyclopentasiloxane, and from about 8% about 40% by weight of silicone polyether.

30. A deodorant composition comprising:
 a) an antimicrobial deodorant active;
 b) a silicone elastomer; and
 c) a volatile silicone;
 wherein the deodorant composition is a single-phase system.

31. A deodorant composition according to claim 30, further comprising a structurant.

32. A deodorant composition according to claim 30, wherein the composition comprises from about 0.01% to about 10% by weight of the deodorant active and from about 0.1% to about 15% by weight of the silicone elastomer.

33. A deodorant composition according to claim 31, wherein the composition comprises from about 0.01% to about 1% by weight of the deodorant active, from about 0.1% to about 15% by weight of the silicone elastomer, and from about 0.1% to about 35% by weight of the structurant.

34. A method of controlling malodor and perspiration comprising the topical application of from about 0.1 gram to about 2.0 gram per axilla of the antiperspirant composition of claim 1.

35. A method of controlling malodor and perspiration comprising the topical application of from about 0.1 gram to about 2.0 gram per axilla of the antiperspirant composition of claim 28.

36. A method of controlling malodor and perspiration comprising the topical application of from about 0.1 gram to about 2.0 gram per axilla of the antiperspirant composition of claim 29.

37. A method of controlling malodor comprising the topical application of from about 0.1 gram to about 2.0 gram per axilla to the axillary of the deodorant composition of claim 30.

38. A method of controlling malodor comprising the topical application of from about 0.1 gram to about 2.0 gram per axilla of the deodorant composition of claim 31.

* * * * *

UNITED STATES PATENT AND TRADEMARK OFFICE
CERTIFICATE OF CORRECTION

PATENT NO. : 6,524,562 B2
DATED : February 25, 2003
INVENTOR(S) : G.J. Guskey

It is certified that error appears in the above-identified patent and that said Letters Patent is hereby corrected as shown below:

Column 8,
Line 39, "oxypropylone" should read -- oxypropylene --.

Signed and Sealed this

Twenty-fourth Day of May, 2005

JON W. DUDAS
*Director of the United States Patent and Trademark Office*